(12) United States Patent
Nanjo et al.

(10) Patent No.: US 12,415,089 B2
(45) Date of Patent: Sep. 16, 2025

(54) PHOTOTHERAPY DEVICE AND METHOD OF OPERATION OF PHOTOTHERAPY DEVICE

(71) Applicant: Teijin Pharma Limited, Tokyo (JP)

(72) Inventors: Takuya Nanjo, Tokyo (JP); Yuki Kawase, Tokyo (JP); Toshihiro Sato, Onomichi (JP); Kazunori Takahashi, Onomichi (JP)

(73) Assignee: Teijin Pharma Limited, Tokyo (JP)

( * ) Notice: Subject to any disclaimer, the term of this patent is extended or adjusted under 35 U.S.C. 154(b) by 513 days.

(21) Appl. No.: 17/635,566

(22) PCT Filed: Aug. 28, 2020

(86) PCT No.: PCT/JP2020/032720
§ 371 (c)(1),
(2) Date: Feb. 15, 2022

(87) PCT Pub. No.: WO2021/040008
PCT Pub. Date: Mar. 4, 2021

(65) Prior Publication Data
US 2022/0296916 A1    Sep. 22, 2022

(30) Foreign Application Priority Data

Aug. 29, 2019  (JP) ................................ 2019-157036
Aug. 29, 2019  (JP) ................................ 2019-157051

(51) Int. Cl.
*A61N 5/067*    (2006.01)
*A61B 17/00*    (2006.01)
(Continued)

(52) U.S. Cl.
CPC ...... *A61N 5/067* (2021.08); *A61N 2005/0626* (2013.01)

(58) Field of Classification Search
CPC ...... A61N 5/06–2005/073; A61B 18/20–18/28
(Continued)

(56) References Cited

U.S. PATENT DOCUMENTS 5,460,182 A * 10/1995 Goodman ............ A61B 5/0084
600/478
2001/0007068 A1    7/2001 Ota et al.
(Continued)

FOREIGN PATENT DOCUMENTS

DE   10 2015 101 880 A1    8/2015
JP       61-23910 A         2/1986
(Continued)

OTHER PUBLICATIONS

International Search Report for PCT/JP2020/032720, dated Nov. 10, 2020 (PCT/ISA/210).

*Primary Examiner* — Benjamin J Klein
*Assistant Examiner* — Vynn V Huh
(74) *Attorney, Agent, or Firm* — Sughrue Mion, PLLC

(57) ABSTRACT

A phototherapy device 1 includes a laser light source 8 for emitting laser light at a target portion T, a limit switch 10 for detecting an approach of the laser light source 8 to a target portion T up to a predetermined distance and outputting a proximity signal, and an optical sensors 7 for detecting a distance to the target portion T and outputting a distance signal S corresponding to the distance and is configured so that a reference value L0 is set based on the distance signal S detected after the proximity signal is detected and emission of laser light by the laser light source 8 is permitted in accordance with an amount of fluctuation of the distance signal S with respect to the reference value L0.

11 Claims, 6 Drawing Sheets

(51) Int. Cl.
*A61B 18/00* (2006.01)
*A61B 18/20* (2006.01)
*A61B 90/00* (2016.01)
*A61N 5/06* (2006.01)

(58) Field of Classification Search
USPC .................................... 607/88–94; 606/2–19
See application file for complete search history.

(56) References Cited

U.S. PATENT DOCUMENTS

| | | | |
|---|---|---|---|
| 2007/0217199 A1* | 9/2007 | Adam | A61N 5/0616 |
| | | | 362/276 |
| 2010/0152718 A1* | 6/2010 | Fujikawa | A61B 18/203 |
| | | | 606/9 |
| 2013/0190845 A1 | 7/2013 | Liu et al. | |
| 2015/0224332 A1 | 8/2015 | Hewitson | |
| 2019/0015681 A1* | 1/2019 | Pyun | A61N 5/0616 |

FOREIGN PATENT DOCUMENTS

| | | |
|---|---|---|
| JP | 63-182764 U | 11/1988 |
| JP | 2000-334053 A | 12/2000 |
| JP | 2000-342702 A | 12/2000 |
| JP | 2012-231978 A | 11/2012 |
| JP | 2013-509222 A | 3/2013 |
| JP | 2016-512783 A | 5/2016 |
| WO | 2005/092438 A1 | 10/2005 |
| WO | 2011/051730 A1 | 5/2011 |
| WO | 2012/150721 A1 | 11/2012 |
| WO | 2014/147624 A1 | 9/2014 |
| WO | 2015/181102 A1 | 12/2015 |

\* cited by examiner

PHOTOTHERAPY DEVICE AND METHOD OF OPERATION OF PHOTOTHERAPY DEVICE

CROSS REFERENCE TO RELATED APPLICATIONS

This application is a National Stage of International Application No. PCT/JP2020/032720, filed Aug. 28, 2020, claiming priority based on Japanese Patent Application No. 2019-157036, filed Aug. 29, 2019, and Japanese Patent Application No. 2019-157051, filed Aug. 29, 2019.

FIELD

The present invention relates to a phototherapy device and a method of operation of a phototherapy device.

BACKGROUND

Phototherapy devices can be used to emit laser light at living tissue for the purpose of promoting blood circulation, promoting the metabolism, and other therapy or assisted therapy. In particular, in the laser classes in the JIS C 6802 safety standards for lasers, if using a class 3 or higher high output phototherapy device for home therapy, compliance with class 1C becomes an essential requirement. In class 1C, it is sought to limit exposure to parts other than the intended target tissue. For this reason, a phototherapy device has to have an interlock mechanism so as to stop emission of laser light if a probe provided with a laser light source of the phototherapy device and a predetermined location of the skin of the target tissue become separated by exactly a predetermined distance, for example, 12 mm, corresponding to one finger's worth of distance.

In this regard, there is known a phototherapy device configured to detect a distance between a probe or laser light source and the skin etc. by an optical sensor etc. and to control emission of laser light in accordance with the detection value, that is, by whether the detection value is within a predetermined allowable range (PTL 1 and PTL 2).

CITATION LIST

Patent Literature

PTL 1: Japanese Unexamined Patent Publication No. 2016-512783
PTL 2: Japanese Unexamined Patent Publication No. 2013-509222

SUMMARY

Technical Problem

According to the detection method by the phototherapy device described in PTL 1 and PTL 2, if the portion or condition of the skin which is targeted, that is, the color or amount of moisture of the skin, extent of wrinkles, etc. differs, the detection value will also differ. This will occur even more so if the subjects differ, but can also occur with the same subject. Therefore, it is necessary to adjust the settings for emission of laser light one by one in accordance with the detection values. Further, in the phototherapy device described in PTL 1, if the sensor is tilted with respect to the skin, sometimes the distance between the laser light source and target tissue will be mistakenly detected. Furthermore, realization of an optical displacement sensor for measuring focal point deviation demands an advanced optical system resulting in a higher manufacturing cost. Therefore, it has been desirable to be able to suitably emit laser light by a simple method not dependent on the subject and the portion and condition of the skin etc.

An optical sensor has a light emitting part emitting light to a target portion and a light receiving part receiving light reflected from the target portion. In a phototherapy device, if using an optical sensor, sometimes light of reflection of the laser light of the laser light source from the target portion ends up being mistakenly detected and an accurate distance signal corresponding to the distance to the target portion cannot be obtained. As a result, it becomes impossible to accurately measure the distance to the target portion and is impossible to suitably emit laser light.

The present invention has as its object to provide a phototherapy device able to suitably emit laser light. More particularly, the present invention provides a phototherapy device able to accurately measure a distance to a target portion and suitably emit laser light.

Solution to Problem

According to one aspect of the present invention, there is provided a phototherapy device comprising a laser light source for emitting laser light at a target portion, a proximity detection part for detecting an approach of the laser light source to a target portion up to a predetermined distance and outputting a proximity signal, and a distance detection part for detecting a distance to the target portion and outputting a distance signal corresponding to the distance and configured so that a reference value is set based on the distance signal detected after the proximity signal is detected and emission of laser light by the laser light source is permitted in accordance with an amount of fluctuation of the distance signal with respect to the reference value.

According to another aspect of the present invention, there is provided a method of operation of a phototherapy device comprising a step of detecting an approach of a laser light source to a target portion up to a predetermined distance and outputting a proximity signal, a step of detecting a distance to the target portion and outputting a distance signal corresponding to the distance, a step of setting a reference value based on the distance signal detected after the proximity signal is detected, and a step of permitting emission of laser light by the laser light source in accordance with an amount of fluctuation of the distance signal with respect to the reference value.

Emission of laser light by the laser light source may be permitted when the distance signal is within a predetermined range with respect to the reference value. Emission of laser light by the laser light source may be prohibited if the distance signal becomes outside the predetermined range with respect to the reference value. The reference value may be reset if the distance signal becomes outside the predetermined range with respect to the reference value. The distance detection part may have a plurality of detection parts and the distance to the target portion may be successively detected by the plurality of detection parts. The distance detection part may have a plurality of detection parts and the reference value may be set based on a plurality of the distance signals by the plurality of detection parts when the plurality of the distance signals are within a predetermined deviation. In emission of laser light by the laser light source, a laser emission period and laser stopping period may be alternately repeated, the distance detection part may have an optical sensor having a light emitting part emitting light to a target portion and a light receiving part receiving light reflected from the target portion, and the light emission and the light reception may be performed in the laser stopping period. The distance detection part may output the distance signal based on a difference between a detection value of reception by the light receiving part of light reflected from the target portion when light is emitted by the light emitting part and a detection value of reception by the light receiving part of light reflected from the target portion when light is not emitted by the light emitting part. The proximity detection part may have a contact type sensor. The device may further comprise a probe, the probe may have the laser light source, proximity detection part, distance detection part, body part, and a moving part able to move in an axial direction of the body part by pressing against the target portion, the proximity detection part may be arranged so as to detect approach of the laser light source to the target portion up to a predetermined distance by relative movement of the body part and the moving part, and the distance detection part may be arranged at the moving part.

Further, according to still another aspect of the present invention, there is provided a phototherapy device comprising a laser light source for emitting laser light at a target portion and a distance detection part for detecting a distance to the target portion and outputting a distance signal corresponding to the distance and configured so that, in emission of laser light by the laser light source, a laser emission period and laser stopping period are alternately repeated, the distance detection part has an optical sensor having a light emitting part emitting light to the target portion and a light receiving part receiving light reflected from the target portion, the light emission and the light reception are performed in the laser stopping period, and emission of laser light by the laser light source is permitted in accordance with the amount of fluctuation of the distance signal.

According to still another aspect of the present invention, there is provided a method of operation of a phototherapy device comprising a step, in emission of laser light of a laser light source where a laser emission period and a laser stopping period are alternately repeated, of detecting a distance to a target portion and outputting a distance signal corresponding to the distance by emitting light to the target portion and receiving light reflected from the target portion in the laser stopping period and a step of permitting emission of laser light by the laser light source in accordance with the amount of fluctuation of the distance signal.

At least part of a laser wavelength of the laser light source may be included in a light reception wavelength of the light receiving part of the distance detection part. The light receiving part of the distance detection part may be further configured to detect light of reflection of the laser light of the laser light source from the target portion. A reference value may be set based on the distance signal, and emission of laser light by the laser light source may be permitted when the distance signal is within a predetermined range with respect to the reference value. Emission of laser light by the laser light source may be prohibited if the distance signal becomes outside the predetermined range with respect to the reference value. The reference value may be reset if the distance signal becomes outside the predetermined range with respect to the reference value. The distance detection part may have a plurality of detection parts and the reference value may be set based on a plurality of the distance signals by the plurality of detection parts when the plurality of the distance signals are within a predetermined deviation. The distance detection part may have a plurality of detection parts and the distance to the target portion may be successively detected by the plurality of detection parts. The distance detection part may output the distance signal based on a difference between a detection value of reception by the light receiving part of light reflected from the target portion when light is emitted by the light emitting part and a detection value of reception by the light receiving part of light reflected from the target portion when light is not emitted by the light emitting part.

Advantageous Effects of Invention

According to these aspects of the present invention, the common effect is exhibited of being able to provide a phototherapy device able to suitably emit laser light.

DESCRIPTION OF EMBODIMENTS

Figure 1:
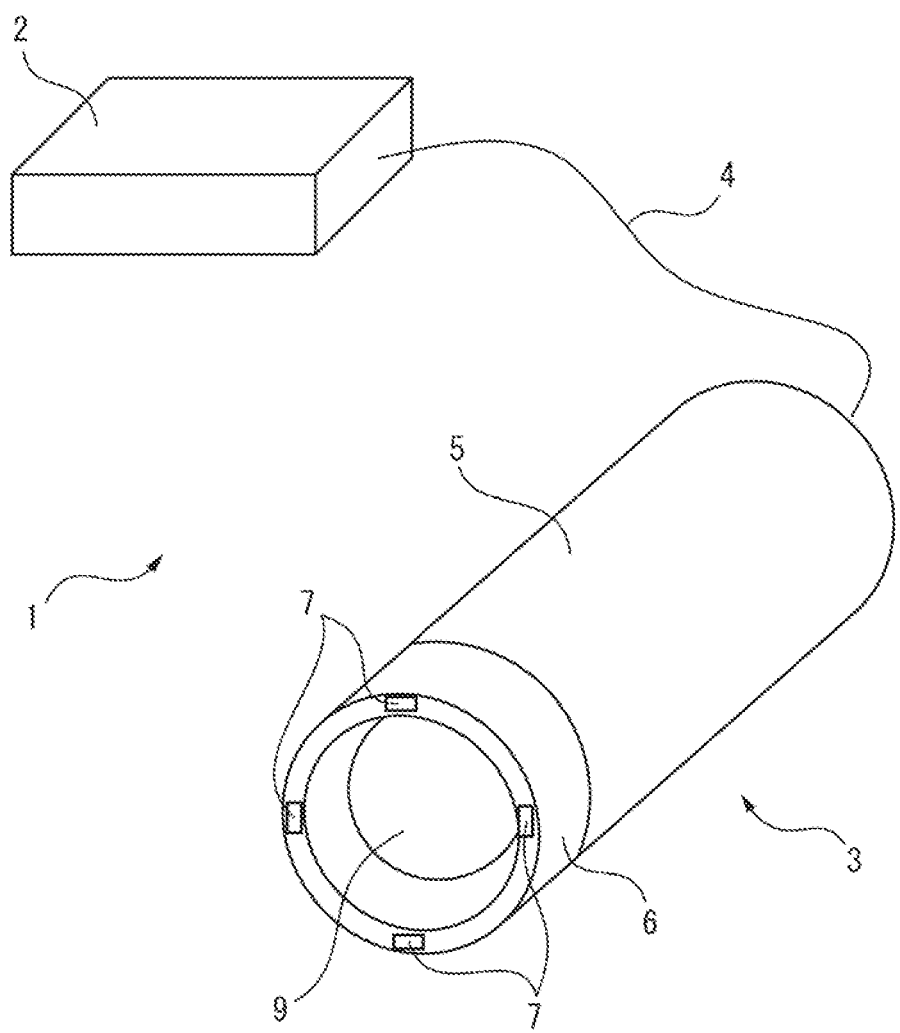
FIG. 1 is a schematic view of a phototherapy device according to an embodiment of the present invention.

Below, while referring to the drawings, embodiments of the present invention will be explained in detail. Throughout the drawings, corresponding component elements will be assigned common reference notations.

Figure 2:
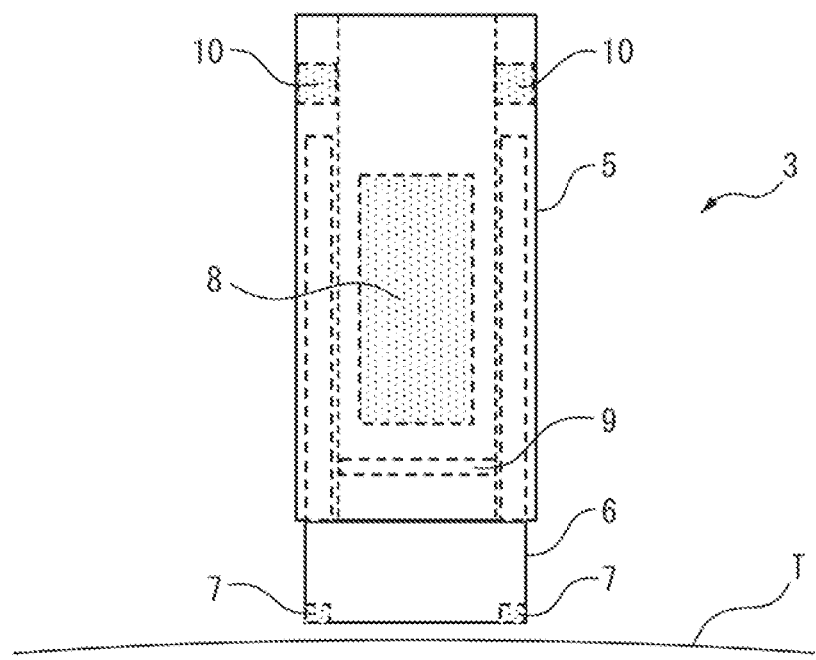
FIG. 2 is a view showing an operation of a probe.

FIG. 1 is a schematic view of a phototherapy device 1 according to an embodiment of the present invention, while FIG. 2 is a view showing an operation of a probe 3.

The phototherapy device 1 has a control device 2, probe 3, and cable 4 electrically connecting the control device 2 and probe 3. The control device 2 has one or more processors, a storage part and its peripheral circuits, etc. The control device 2 comprehensively controls the overall operation of the probe 3 such as shown in the later explained flow chart based on a computer program stored in advance in the storage part. At the time of this processing, the control device 2 receives signals of various sensors such as the later explained optical sensors etc. and sends control signals relating to emission and stopping of the laser light source etc. The control device 2 may also have an input/output part, for example, a display or other display part, and operating buttons or a touch screen or other input interface.

The probe 3 has a cylindrical body part 5, a cylindrical moving part 6 arranged inside the body part 5 to be able to move along an axial direction of the body part 5, four optical sensors 7 provided at a front end face of the moving part 6, a laser light source 8 arranged at an inside of the body part 5, an optical window 9 provided at a front surface of the body part 5, and a limit switch 10 arranged inside the body part 5. The moving part 6 is biased by a not shown elastic member to the front with respect to the body part 5.

The optical sensors 7 and the limit switch 10 are arranged at the inside of the probe 3 and are arranged so as not to directly contact the skin etc. Due to this, there is little risk of the optical sensors 7 and the limit switch 10 having skin oil or dirt etc. deposit on them and stable performance can be maintained. Further, the optical sensors 7 and the limit switch 10 are arranged so as not to obstruct movement of the moving part 6 and emission of laser light by the laser light source 8.

In the laser classes in the JIS C 6802 safety standards for lasers, if using a phototherapy device 1 mounting a class 3 or higher high output laser light source 8 for home therapy, the phototherapy device 1 must comply with class 1C, but the invention is not limited to this. It is possible to use a laser light source 8 complying with home therapy by other standards as well.

Figure 2B:
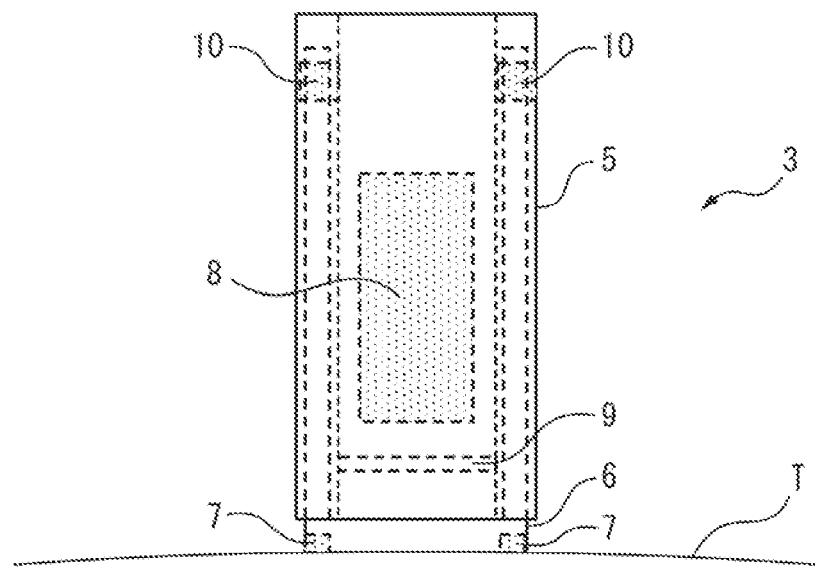

FIG. 2(A) shows the state before pressing the probe 3 against the living target tissue, that is, the target portion T, while FIG. 2(B) shows the state when pressing the probe 3 against the target portion T. If pressing the probe 3 against the target portion T from the state shown in FIG. 2(A), the moving part 6 retracts and the limit switch 10 becomes ON (FIG. 2(B)). That is, the limit switch 10 configures a proximity detection part which detects the approach of the laser light source 8 to the target portion T up to a predetermined distance and outputs a proximity signal. The output proximity signal is detected by the control device 2. On the other hand, if removing the pressing force of the probe 3 against the target portion T, the moving part 6 retracts due to the biasing force of the elastic member and the limit switch 10 becomes OFF (FIG. 2(A)).

The four optical sensors 7 are arranged at the front end face of the moving part 6 at equal intervals along the circumferential direction. Note that, the phototherapy device 1 may also be made to have one, two, or three optical sensors 7 and may be made to have five or more optical sensors 7. If the phototherapy device 1 has a plurality of optical sensors 7, the plurality of optical sensors 7 are preferably arranged at equal intervals along the circumferential direction. Each of the one or more optical sensors 7 configures a detection part. Overall, they configure a distance detection part for detecting a distance up to the target portion T and outputting distance signals corresponding to the distance. The output distance signals are detected by the control device 2. Each optical sensor 7 has a not shown light emitting part for emitting light to the target portion T and a not shown light receiving part for receiving light reflected from the target portion T. The optical sensor 7 evaluates the distance to the target portion T by the change of the intensity of the reflected light received by the light receiving part. Using the distance signals, it is possible to for example calculate the distance from the laser light source 8 to the target portion T.

Figure 3:
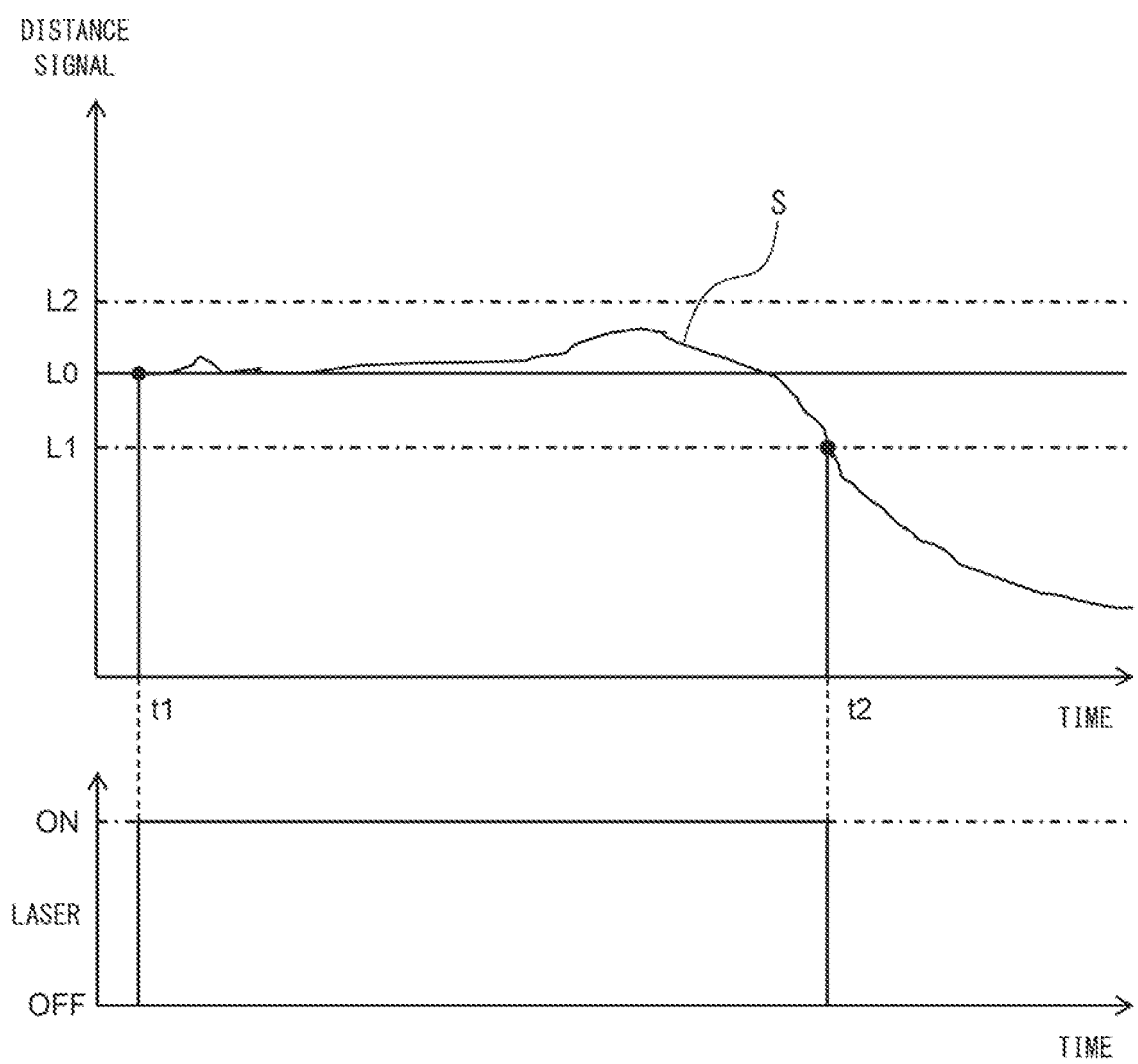
FIG. 3 is a view showing a relationship between a change of a distance signal and emission of laser light.
Figure 4:
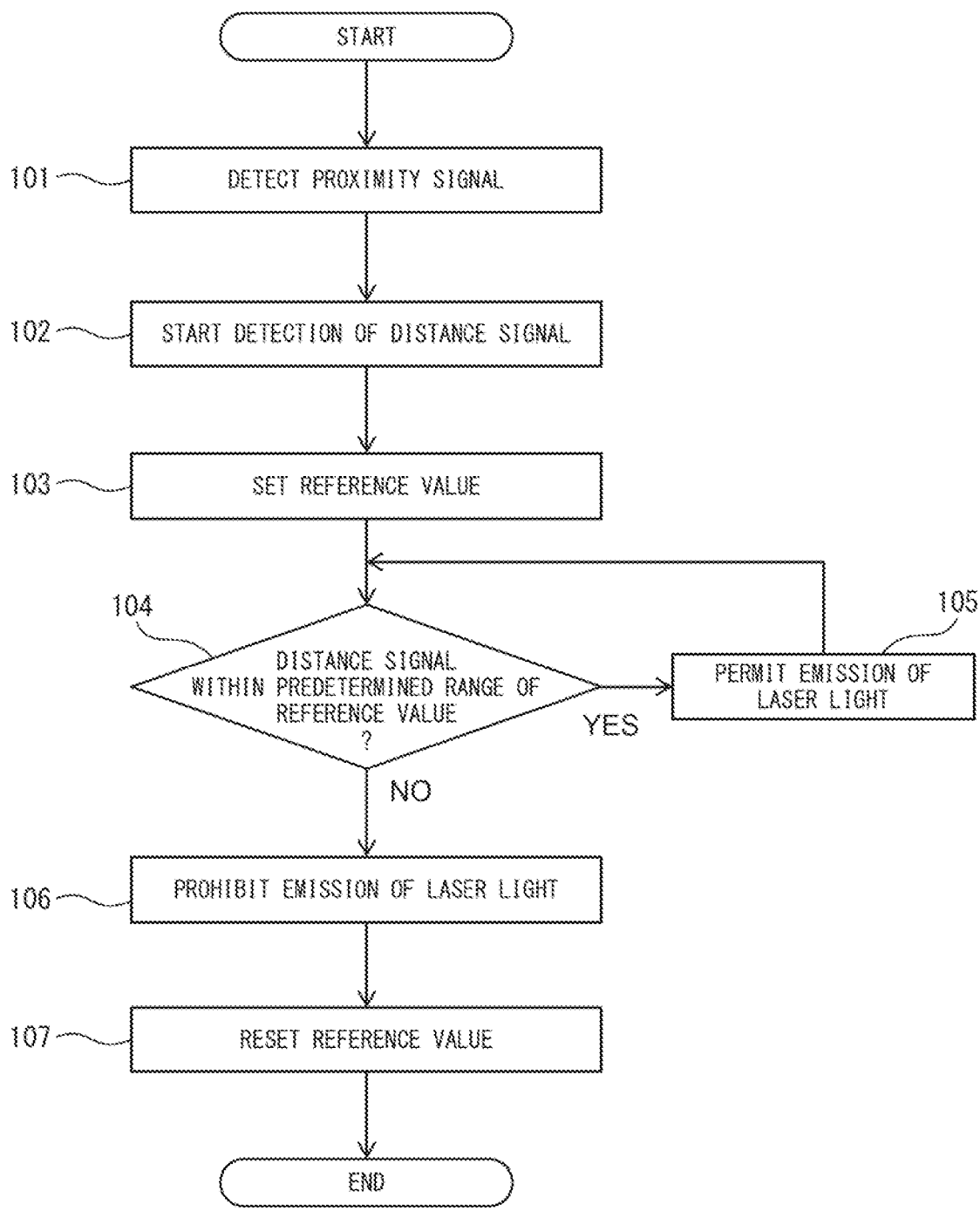
FIG. 4 is a flow chart showing an operation of a phototherapy device.

The operation of the phototherapy device 1 will be explained while referring to FIG. 3 and FIG. 4. FIG. 3 is a view showing the relationship between a change of a distance signal S and emission of laser light. In FIG. 3, the top graph shows the change along with time of the value of the distance signal S of an optical sensor 7 and the bottom graph shows the state of emission of laser light. FIG. 4 is a flow chart showing the operation of the phototherapy device 1.

In FIG. 4, first, at step 101, the user presses the probe 3 against the target portion T whereby a proximity signal output by the limit switch 10 becoming ON is detected. Next, at step 102, the proximity signal triggers the start of detection of the distance signal S output corresponding to the distance up to the target portion T (time t1). Next, at step 103, a reference value L0 is set based on the distance signal S detected after the limit switch 10 becomes ON, that is, after a proximity signal is detected. Next, at step 104, it is judged if the distance signal S is within a predetermined range with respect to the reference value L0, that is, is in a range between a lower limit L1 and an upper limit L2. If the distance signal S is within a predetermined range with respect to the reference value L0, the routine proceeds to step 105, where emission of laser light of the laser light source 8 to the target portion T is permitted and the laser light is emitted.

On the other hand, if at step 104 a change of the position and posture of the probe 3 with respect to the target portion T etc. causes the distance signal S to become outside a predetermined range from the reference value L0 (time t2), the routine proceeds to step 106. Next, at step 106, emission of laser light by the laser light source 8 is prohibited. Therefore, if emitting laser light through step 105, emission of the laser light is stopped. Next, at step 107, the reference value L0 set at step 103 is reset and operation of the phototherapy device 1 is ended.

Here, the reference value L0 is set based on the distance signal S of an optical sensor 7, but any method may be used to set the reference value L0. For example, after a proximity signal is detected, the average value obtained by sampling the signals of the four optical sensors 7 for a predetermined time period may be used as the distance signal S and this may be set as the reference value L0. Further, the average value may be used as the distance signal S and this set as the reference value L0 only if all of the distance signals S of the four optical sensors 7 fall within a predetermined deviation. If not falling within a predetermined deviation, even if a proximity signal is detected, the operation of the phototherapy device 1 may be ended without setting the reference value L0.

If each of the distance signals S of the four optical sensors 7 does not fall within a predetermined deviation, for example, sometimes the probe 3 will be pressed against the target portion T in a tilted state. In this case, part of the front end of the moving part 6 of the probe 3 will abut against the target portion T and the opposite side part will separate from the target portion T. Therefore, all of the distance signals S of the plurality of optical sensors 7 arranged at equal intervals along the circumferential direction will greatly differ from each other. If emitting laser light in this state, the laser light would be emitted to parts other than the target portion T, so emission of laser light has to be prohibited. Therefore, it is effective to judge if the plurality of distance signals S fall within a predetermined deviation.

The predetermined range with respect to the reference value L0, as shown in FIG. 3, is a range between the lower limit L1 and upper limit L2. The lower limit L1 and upper limit L2 are, for example, ±5% with respect to the reference value and are set by ratios with respect to the reference value. The upper limit L2 and lower limit L1 are determined considering the effect of therapy and safety etc. For example, the lower limit L1 is determined by whether the laser light source 8 separates from the target portion T and the possibility arises of emission to a part other than the target portion. That is, the relationship between the reflected light of the optical sensors 7 and the distance to the subject may be found in advance and, for example, the ranges of the upper and lower limits may be set based on the amount of displacement of the reflected light corresponding to an interval of 12 mm, equivalent to one fingers worth of distance. A distance signal S being outside a predetermined range with respect to the reference value L0 means a state where a gap is formed to greater than or equal to an allowable range. There is a possibility of a finger ending up entering the gap. As a result, the high output laser light ends up being emitted at living tissue other than the target portion T. Note that, the lower limit L1 and upper limit L2 may be set by absolute values rather than ratios with respect to the reference value. Further, to judge only the laser light source 8 moving away from the target portion T, the upper limit L2 need not be set. It is sufficient to set only the lower limit L1.

Note that, the reference value L0 may also be set based on distance signals S measured in advance etc. without being triggered by the proximity signal. That is, in the phototherapy device 1, the limit switch 10 may be omitted.

Figure 5:
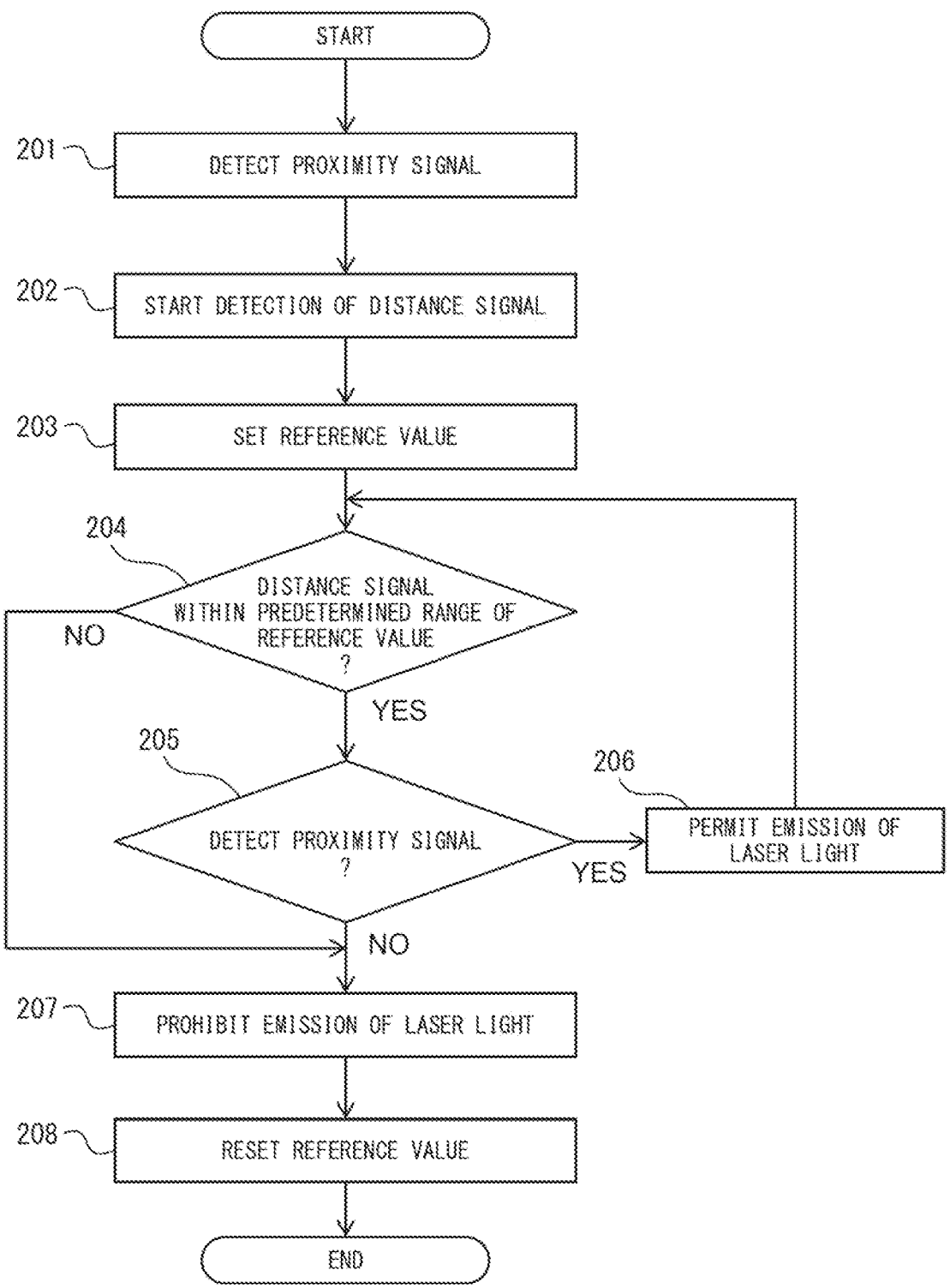
FIG. 5 is a flow chart showing another operation of a phototherapy device.

FIG. 5 is a flow chart showing another operation of the phototherapy device 1. In FIG. 5, first, at step 201, the user presses the probe 3 against the target portion T whereby a proximity signal output by the limit switch 10 becoming ON is detected. Next, at step 202, the proximity signal triggers the start of detection of a distance signal S output corresponding to the distance up to the target portion T (time t1). Next, at step 203, the reference value L0 is set based on the distance signal S detected after the limit switch 10 becomes ON, that is, after a proximity signal is detected. Next, at step 204, it is judged if the distance signal S is within a predetermined range with respect to the reference value L0, that is, is in the range between the lower limit L1 and upper limit L2. If the distance signal S is within a predetermined range with respect to the reference value L0, the routine proceeds to step 205. Next, at step 205, it is judged if a proximity signal showing that the limit switch 10 is ON is detected. If a proximity signal is detected, the routine proceeds to step 206 where emission of laser light of the laser light source 8 to the target portion T is permitted and the laser light is emitted.

On the other hand, if at step 204 a change of the position and posture of the probe 3 with respect to the target portion T etc. causes the distance signal S to become outside a predetermined range from the reference value L0 (time t2), the routine proceeds to step 207. Similarly, if at step 205 a proximity signal was not detected, the routine proceeds to step 207. Next, at step 207, emission of laser light by the laser light source 8 is prohibited. Therefore, if laser light is emitted through step 206, emission of laser light is stopped. Next, at step 208, the reference value L0 set at step 203 is reset and operation of the phototherapy device 1 is ended.

The operation of the phototherapy device 1 shown in the flow chart of FIG. 4 and the operation of the phototherapy device 1 shown in the flow chart of FIG. 5 differ only on the point that it is continued to be judged if a proximity signal is detected, that is, if the limit switch 10 is ON, after the start of emission of laser light. Note that, in the operation of the phototherapy device 1 shown in the flow chart of FIG. 4, as a routine performed by interruption every predetermined set time period, it is also possible that it be judged if the limit switch 10 be ON and a proximity signal is detected after the start of emission of laser light. By judging if a proximity signal is detected even after the start of emission of laser light, it is possible to detect when the probe 3 unintentionally ends up moving away from the target portion T. Due to this, it is possible to prevent laser light from being emitted to a part other than the target portion T and to more suitably emit laser light.

According to the phototherapy device 1, the reference value L0 is set based on the distance signal S detected after a proximity signal is detected and laser light is emitted by the laser light source 8 in accordance with the amount of fluctuation of the distance signal S with respect to the reference value L0. Therefore, the laser light source 8 sufficiently approaches the target portion T, so it is possible to reliably emit laser light to only the target portion T. Laser light is never emitted to a part other than the target portion T. Further, according to the phototherapy device 1, the reference value L0 is set in accordance with the target portion T, so if the portion or condition of the skin targeted, that is, the color or amount of moisture of the skin, extent of wrinkles, etc. differ, the reference value L0 which is set also differs. Further, the predetermined range defined by the lower limit L1 and upper limit L2 with respect to the reference value L0 also differs. Therefore, there is no need to adjust the settings for emission of laser light one by one in accordance with the target portion T. As a result, according to the phototherapy device 1, it is possible to suitably emit laser light.

Furthermore, in the phototherapy device 1, if the distance signal S becomes outside the predetermined range with respect to the reference value L0, emission of laser light is stopped. The reference value L0 is set in accordance with the target portion T, so according to the phototherapy device 1, an interlock mechanism is realized able to handle a target portion T of various portions or conditions of the skin. For example, the lower limit L1 and upper limit L2 corresponding to the reference value L0 may be set in advance so as to stop emission of laser light if the probe 3 moves away from the target portion T by exactly a predetermined distance, for example, by exactly a distance of 12 mm, corresponding to one finger's worth of distance. Due to this, stopping laser light due just because a user changes holding position of the probe 3 or moves the probe 3 can be prevented and a drop in the therapy adherence can be prevented. The prohibition of emission of laser light may also be performed by detecting abnormalities in temperature etc. of the probe 3 in addition to the proximity signal and distance signal.

In this regard, in the phototherapy device 1, if using an optical sensor 7 as the distance detection part, sometimes light of reflection of the laser light of the laser light source 8 from the target portion T may end up being mistakenly detected by the optical sensor 7 and an accurate distance signal corresponding to the distance up to the target portion T may not be able to be obtained. As a result, the distance up to the target portion T can no longer be accurately measured or laser light cannot be suitably emitted. This will be explained while referring to FIG. 6.

Figure 6:
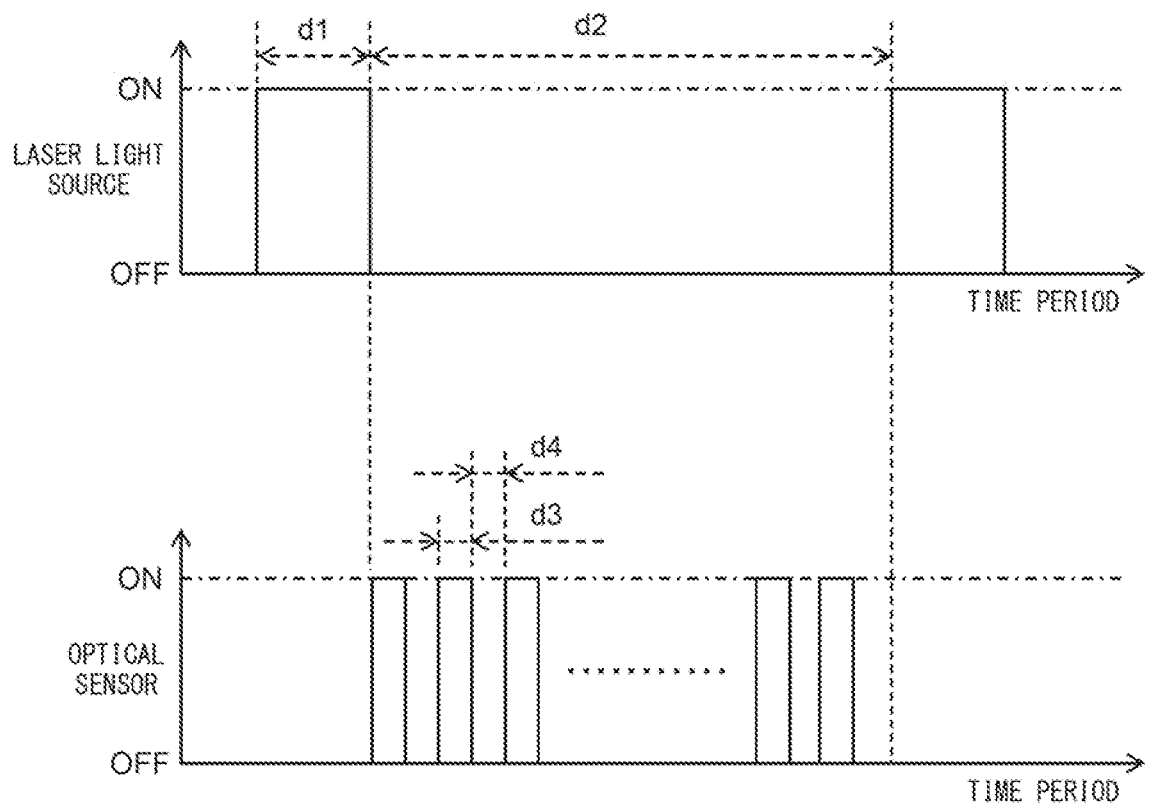
FIG. 6 is a view showing a relationship between emission of laser light and detection of a distance signal.

FIG. 6 is a view showing the relationship between the emission of laser light and detection of a distance signal S. In FIG. 6, the top graph shows the ON or OFF timing of emission of laser light by the laser light source 8, while the bottom graph shows the ON or OFF timing of detection by the optical sensor 7.

In the phototherapy device 1, the laser light is emitted by the laser light source 8 not by a continuous wave (CW), but by a pulse wave (PW). Therefore, in emission of laser light by the laser light source 8, the laser emission period d1 and laser stopping period d2 are alternately repeated. Due to this, it is possible to easily suppress a rise of temperature of the target portion due to emission of laser light. The laser emission period d1 is for example 20 ms, while the laser stopping period d2 is, for example, 180 ms.

Note that, it is also possible to use a laser light source having an output waveform of a continuous wave (CW) and perform control so that a laser emission period and a laser stopping period are alternately repeated by a cycle sufficiently longer than the case of a pulse wave (PW). Note that, it is also possible to not provide a laser emission period and laser stopping period but to perform continuous wave oscillation (CW). The time period shown in FIG. 3 where the laser is ON shows the state where emission of laser light is permitted. The generated laser light may be a continuous wave (CW) or pulse wave (PW) in that time period.

The optical sensor 7 detects light by the light emitting part emitting light to the target portion T and the light receiving part receiving light reflected from the target portion T when the optical sensor 7 is ON. If the time period when the optical sensor 7 is ON, that is, the detection period, is d3 and the time period when the optical sensor 7 is OFF, that is, the stopping period is d4, d3 and d4 are for example 1 ms. The detection by the optical sensor 7, that is, the light emission by the light emitting part and light reception by the light receiving part, is performed in the laser stopping period d2. Due to this, an accurate distance signal corresponding to the distance to the target portion is obtained and the distance to the target portion can be accurately measured without the optical sensor 7 ending up detecting light of reflection of the laser light of the laser light source 8 from the target portion T. As a result, it is possible to suitably emit laser light.

At the phototherapy device 1, the light receiving part is configured so that all or at least part of the laser wavelength of the laser light source 8 is included in the received wavelength of the light receiving part of the optical sensor 7. Due to this, there is no longer any restriction on the specifications of the light receiving element mounted at the optical sensor 7, and an inexpensive, high quality light receiving element can be selected.

Further, in the detection of the distance to the target portion T by the optical sensor 7 performed at the laser stopping period d2, four optical sensors 7 may also simultaneously detect the distance at the timing shown in FIG. 6. However, the four optical sensors 7 may also perform the detection operations successively. That is, the light emission and light reception at one optical sensor 7 may be performed at a timing not overlapping the light emission and light recession of another optical sensor 7. Due to this, it is possible to prevent light reflected from the target portion by light emission of another optical sensor 7 from ending up being received. The detection operation of the optical sensor 7 may be performed over the entire laser stopping period d2 or may be performed at part of the laser stopping period d2.

Figure 7:
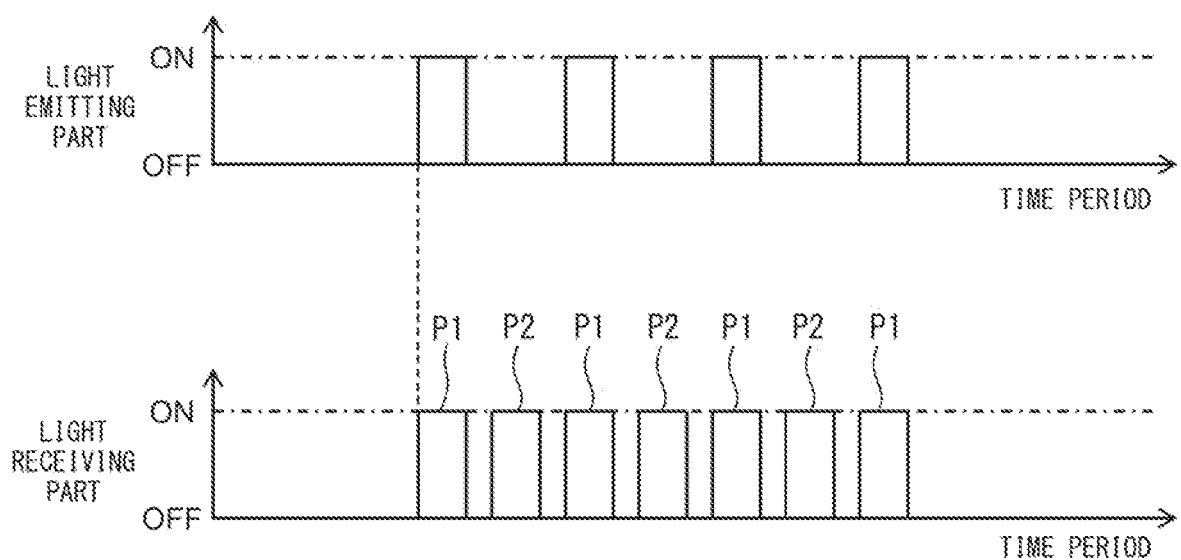
FIG. 7 is a view showing a relationship of operations of a light emitting part and light receiving part.

Next, while referring to FIG. 7, accurate detection by an optical sensor 7 will be explained. FIG. 7 is a view showing the relationship between operations of the light emitting part and light receiving part. In FIG. 7, the top graph shows the ON or OFF timing of light emission by the light emitting part while the bottom graph shows the ON or OFF timing of light reception by the light receiving part.

As shown in FIG. 7, in the optical sensor 7, the light receiving part receives light reflected from the target portion T at the period P1 of the same timing as light emission by the light emitting part and receives light reflected from the target portion T as well at the period P2 of a timing between one light emission by the light emitting part and next light emission. Therefore, the optical sensor 7 outputs a distance signal S based on the difference between a detection value of reception by the light receiving part of light reflected from the target portion T when light is emitted by the light emitting part and a detection value of reception by the light receiving part of light reflected from the target portion T when light is not emitted by the light emitting part.

If at an optical sensor 7 the light receiving part were to receive light reflected from the target portion T only at the period P1 of a timing the same as light emission by the light emitting part, when stray or ambient light entered from between the optical sensor 7 and the target portion T, the detection value would appear to increase and the accurate distance could not be measured. On the other hand, by making the light receiving part at the optical sensor 7 further receive light reflected from the target portion T also at the period P2 of a timing between light emission by the light emitting part and the next light emission, it would be possible to learn the apparent increase at the time of detection. Therefore, by acquiring the difference between the detection values of the light receiving part at the period P1 and the period P2, it would be possible to remove the amount of change due to stray light etc. and possible to obtain an optical sensor 7 resistant to outside disturbances.

The light receiving part of an optical sensor 7 can further be configured to detect light of reflection of the laser light of the laser light source 8 from the target portion T. That is, the light receiving part of the optical sensor 7 can be made to operate at all times or at least when the laser light source 8 is emitting laser light to thereby detect light of reflection of the laser light of the laser light source 8 from the target portion T as well. Due to this, it is possible to measure the emission time of the laser light by the laser light source 8 and possible to confirm the presence of laser light emission.

In the above embodiment, as the proximity detection part, a limit switch 10 was used, but so long as it can detect the approach of the laser light source 8 with respect to the target portion T up to a predetermined distance and output a proximity signal, it may also be another sensor etc. So long as it can sense contact of the moving part 6 with respect to the skin or retraction of the moving part 6, it may also be another contact type sensor. By making it a contact type sensor, it is possible to eliminate the effect of the portion or condition etc. of the skin.

As the distance detection part, an optical sensor 7 was used, but so long as able to detect a distance to a target portion T and output a distance signal S corresponding to the distance, it may also be another sensor etc. However, considering the expense and performance, the distance detection part is preferably an optical sensor, as explained above. An optical sensor enables measurement without contact, so the risk of skin oil or dirt etc. being deposited on it is small and stable performance can be maintained.

The proximity detection part and distance detection part may be respectively selected from optical sensors, electrostatic capacity sensors, temperature sensors, ultrasonic sensors, audio sensors, microwave sensors, and physical sensors. To raise the ruggedness of the phototherapy device 1, the proximity detection part and distance detection part are preferably different types of sensors from each other. Further, the proximity detection part may be configured from a plurality of sensors of the same or different types from each other. Similarly, the distance detection part may be configured from a plurality of sensors of the same or different types from each other.

In the above-mentioned phototherapy device 1, the limit switch 10, that is, the proximity detection part, may also be omitted. In this case, the phototherapy device may be provided with a laser light source for emitting laser light at a target portion and a distance detection part for detecting a distance to the target portion and outputting a distance signal corresponding to the distance and be configured so that in the emission of laser lightly the laser light source, a laser emission period and laser stopping period are alternately repeated, the distance detection part has an optical sensor having a light emitting part emitting light to the target portion and a light receiving part receiving light reflected from the target portion, the light emission and the light reception are performed in the laser stopping period, and laser light is emitted by the laser light source in accordance with the amount of fluctuation of the distance signal.

REFERENCE SIGNS LIST 1. phototherapy device
2. control device 3. probe
4. cable
5. body part
6. moving part
7. optical sensor
8. laser light source
9. optical window
10. limit switch
S. distance signal
T. target portion
L0. reference value
L1. lower limit
L2. upper limit
d1. laser emission period
d2. laser stopping period

The invention claimed is:

1. A phototherapy device comprising:
a laser light source for emitting laser light at a target portion;
a cylindrical body part housing the laser light source therein;
a proximity detection part comprising a moving part and a switch, wherein the proximity detection part is configured to detect an approach of the laser light source to a target portion based on the moving part being pressed against the target portion and retracting into the cylindrical body part up to a predetermined distance and the switch becoming ON, and to output a proximity signal indicating that the moving part is retracted into the cylindrical body part up to the predetermined distance; and
a distance detection part, different from the proximity detection part, comprising one or more optical sensors;
wherein the phototherapy device is configured to:
based on the proximity signal being output from the proximity detection part, start to detect, by the one or more optical sensors, a distance to the target portion and to output a distance signal corresponding to the distance;
adjust a reference value based on the distance signal detected after determining that the proximity signal is detected; and
signal that emission of laser light by the laser light source is permitted in accordance with an amount of fluctuation of the distance signal with respect to the adjusted reference value.

2. The phototherapy device according to claim 1, wherein emission of laser light by the laser light source is permitted when the distance signal is within a predetermined range with respect to the reference value.

3. The phototherapy device according to claim 2, wherein emission of laser light by the laser light source is prohibited if the distance signal becomes outside the predetermined range with respect to the reference value.

4. The phototherapy device according to claim 3, wherein the reference value is reset if the distance signal becomes outside the predetermined range with respect to the reference value.

5. The phototherapy device according to claim 1, wherein the distance detection part has a plurality of detection parts and the distance to the target portion is successively detected by the plurality of detection parts.

6. The phototherapy device according to claim 1, wherein the distance detection part has a plurality of detection parts and the reference value is set based on a plurality of the distance signals by the plurality of detection parts when the plurality of the distance signals are within a predetermined deviation.

7. The phototherapy device according to claim 1, wherein in emission of laser light by the laser light source, a laser emission period and laser stopping period are alternately repeated, the distance detection part has an optical sensor having a light emitting part emitting light to a target portion and a light receiving part receiving light reflected from the target portion, and the light emission and the light reception are performed in the laser stopping period.

8. The phototherapy device according to claim 7, wherein the distance detection part outputs the distance signal based on a difference between a detection value of reception by the light receiving part of light reflected from the target portion when light is emitted by the light emitting part and a detection value of reception by the light receiving part of light reflected from the target portion when light is not emitted by the light emitting part.

9. The phototherapy device according to claim 1, wherein the switch of the proximity detection part has a contact type sensor.

10. The phototherapy device according to claim 1, wherein
the device further comprises a probe,
the probe has the laser light source, the proximity detection part, the distance detection part, the body part, and the moving part, wherein the moving part is configured to move in an axial direction of the body part by pressing against the target portion,
the proximity detection part is arranged so as to detect approach of the laser light source to the target portion up to a predetermined distance by relative movement of the body part and the moving part, and
the distance detection part is arranged at the moving part.

11. A method of operation of a phototherapy device comprising:
a step of detecting, by a proximity detection part, an approach of a laser light source to a target portion based on a moving part of the phototherapy device being pressed against a target portion and retracting into a cylindrical body part of the phototherapy device up to a predetermined distance and the switch becoming ON, and outputting a proximity signal indicating that the moving part is retracted into the cylindrical body part up to the predetermined distance;
a step of detecting by a distance detection part different from the proximity detection part and comprising one or more optical sensors, a distance to the target portion and outputting a distance signal corresponding to the distance, wherein the step of detecting is started based on the proximity signal being output from the proximity detection part;
a step of adjusting a reference value based on the distance signal detected after determining that the proximity signal is detected; and
a step of signaling that emission of laser light by the laser light source is permitted in accordance with an amount of fluctuation of the distance signal with respect to the adjusted reference value.

* * * * *